United States Patent [19]

Beck et al.

[11] Patent Number: 5,675,047
[45] Date of Patent: *Oct. 7, 1997

[54] METHOD OF PREPARATION OF EX SITU SELECTIVATED ZEOLITE CATALYSTS FOR AROMATIC ALKYLATION APPLICATIONS

[75] Inventors: Jeffrey S. Beck, Princeton; Ralph M. Dessau, Edison; David H. Olson, Pennington, all of N.J.

[73] Assignee: Mobil Oil Corporation, Fairfax, Va.

[*] Notice: The term of this patent shall not extend beyond the expiration date of Pat. No. 5,403,800.

[21] Appl. No.: 461,860

[22] Filed: Jun. 5, 1995

Related U.S. Application Data

[63] Continuation-in-part of Ser. No. 69,251, May 28, 1993, Pat. No. 5,476,823.

[51] Int. Cl.⁶ .................................................. C07C 2/68
[52] U.S. Cl. .......................... 585/467; 502/64; 502/71; 502/63
[58] Field of Search .................. 208/86, 257; 585/407, 585/418, 475, 481, 467; 502/63, 64, 71

[56] References Cited

U.S. PATENT DOCUMENTS

| | | |
|---|---|---|
| 3,251,897 | 5/1966 | Wise . |
| 3,257,310 | 6/1966 | Plank et al. . |
| 3,437,587 | 4/1969 | Elbert et al. . |
| 3,682,996 | 8/1972 | Kerr . |
| 3,698,157 | 10/1972 | Allen et al. . |
| 4,016,218 | 4/1977 | Haag et al. . |
| 4,049,738 | 9/1977 | Young . |
| 4,060,568 | 11/1977 | Rodewald . |
| 4,086,287 | 4/1978 | Kaeding et al. . |
| 4,090,981 | 5/1978 | Rodewald . |
| 4,100,215 | 7/1978 | Chen . |
| 4,117,024 | 9/1978 | Kaeding . |
| 4,127,616 | 11/1978 | Rodewald . |
| 4,145,315 | 3/1979 | Rodewald . |
| 4,224,141 | 9/1980 | Morrison et al. . |
| 4,283,306 | 8/1981 | Herkes . |
| 4,326,994 | 4/1982 | Haag et al. . |
| 4,402,867 | 9/1983 | Rodewald . |
| 4,443,554 | 4/1984 | Dessau . |
| 4,465,886 | 8/1984 | Rodewald . |
| 4,477,583 | 10/1984 | Rodewald . |
| 4,487,843 | 12/1984 | Telford et al. . |
| 4,522,929 | 6/1985 | Chester et al. . |
| 4,545,914 | 10/1985 | Chu . |
| 4,559,314 | 12/1985 | Shihabi . |
| 4,843,057 | 6/1989 | D'Amore et al. . |
| 4,851,604 | 7/1989 | Absil et al. . |
| 4,927,979 | 5/1990 | Yamagishi et al. . |
| 4,950,835 | 8/1990 | Wang et al. . |
| 5,173,641 | 12/1992 | Absil et al. . |
| 5,321,183 | 6/1994 | Chang et al. ............... 585/475 |
| 5,349,113 | 9/1994 | Chang et al. ............... 585/475 |
| 5,349,114 | 9/1994 | Lago et al. ................. 585/475 |
| 5,365,003 | 11/1994 | Chang et al. ............... 585/470 |
| 5,367,099 | 11/1994 | Beck et al. ................. 585/475 |
| 5,382,737 | 1/1995 | Beck et al. ................. 585/475 |
| 5,403,800 | 4/1995 | Beck et al. ................... 502/64 |
| 5,406,015 | 4/1995 | Beck et al. ................. 585/475 |
| 5,455,213 | 10/1995 | Chang et al. ................. 502/63 |
| 5,475,179 | 12/1995 | Chang et al. ............... 585/475 |
| 5,476,823 | 12/1995 | Beck et al. ................... 502/60 |
| 5,488,194 | 1/1996 | Beck et al. ................. 585/475 |
| 5,495,059 | 2/1996 | Beck et al. ................. 585/470 |
| 5,498,814 | 3/1996 | Chang et al. ............... 585/475 |
| 5,516,736 | 5/1996 | Chang et al. ............... 585/475 |
| 5,516,956 | 5/1996 | Abchandani et al. ........ 585/481 |
| 5,565,004 | 10/1996 | Beck et al. ................. 585/475 |

FOREIGN PATENT DOCUMENTS 0 296 582A2  6/1988  European Pat. Off. .

OTHER PUBLICATIONS

Nakajima et al., "p–Xylene–Selective Disproportionation of Toluene over a Modified Pentasil Type Zeolite", *Sekiyu Gakkaishi*, 35(2), 185–189 (1992).

Hibino et al., "Shape–Selectivity over HZSM–5 Modified by Chemical Vapor Deposition of Silicon Alkoxide", *Journal of Catalysis*, 128, 551–558 (1991).

Lago et al., "The Nature of the Catalytic Sites in HZSM–5 Activity Enhancement", *New Development in Zeolite Science Technology: Proceeding of the 7th International Zeolite Conference*, 677–684 (1986).

*Primary Examiner*—Michael Lewis
*Assistant Examiner*—Thomas G. Dunn Jr.
*Attorney, Agent, or Firm*—Malcolm D. Keen; Peter W. Roberts

[57] ABSTRACT

The present invention is a method of producing an ex situ selectivated catalytic molecular sieve for shape selective aromatic alkylation in which a catalytic molecular sieve having a reduced activity is modified by being exposed to at least two selectivation sequences, each sequence includes contacting the molecular sieve with a selectivating agent and subsequently calcining the contacted molecular sieve. The present invention is also a method of producing an ex situ selectivated catalytic molecular sieve for shape selective aromatic alkylation in which a catalytic molecular sieve is modified by being exposed to at least two selectivation sequences and then reduced in activity. The ex situ selectivated catalytic molecular sieves may optionally be further modified by in situ trim selectivation. The present invention is also a process for shape selective aromatic alkylation utilizing the modified molecular sieves.

76 Claims, No Drawings

METHOD OF PREPARATION OF EX SITU SELECTIVATED ZEOLITE CATALYSTS FOR AROMATIC ALKYLATION APPLICATIONS

CROSS-REFERENCE TO RELATED APPLICATIONS

This is a continuation-in-part of application Ser. No. 08/069,251 filed on May 28, 1993 now U.S. Pat. No. 5,476,823. The entire disclosure of the above-cited application is expressly incorporated herein by reference.

BACKGROUND OF THE INVENTION

The present invention relates to modified catalytic molecular sieves and a method for their production. The invention also relates to the shape-selective aromatic alkylation processes over the modified catalytic molecular sieves.

The term "shape-selective catalysis" describes the unexpected catalytic selectivities found in catalytic molecular sieves, i.e., zeolite catalysts. The principles behind shape-selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in alkylation of an alkylbenzene to a para-dialkylbenzene.

A representative para-dialkylbenzene is para-xylene. The production of para-xylene is typically performed by the methylation of toluene over a catalyst under conversion conditions. An example of this reaction of toluene with methanol, is described in Chen et al., J. Amer. Chem. Soc. 101, 6783 (1979). Such a method typically results in the production of a mixture of the three xylene isomers, i.e., para-xylene, ortho-xylene, and meta-xylene. The three xylene isomers are typically found in the following equilibrium ratio: 24 wt. % para-xylene; 54 wt. % meta-xylene and 22 wt. % ortho-xylene.

However, depending upon the degree of selectivity of the catalyst for para-isomer of xylene (i.e., para-selectivity) and the reaction conditions, different percentages of para-xylene are obtained. The yield, i.e., the amount of xylene produced as a proportion of the feedstock, is also affected by the catalyst and the reaction conditions.

In order to increase the para-selectivity of zeolite catalysts various methods, as known in the art, have been utilized. One such method is to modify the catalyst by treatment with a "selectivating agent". For example, U.S. Pat. Nos. 5,173,461, 4,950,835, 4,927,979, 4,465,886, 4,477,583, 4,402,867 4,379,761, 4,145,315, 4,127,616, 4,100,215, 4,090,981, 4,060,568 and 3,698,157 disclose specific methods for contacting a catalyst with a selectivating agent containing silicon ("silicon compound").

However, the ex situ selectivation of zeolites in the prior art has mostly involved single applications of a modifying compound. In one case where multiple treatments were utilized, para-selectivity actually decreased. U.S. Pat. No. 4,283,306 to Herkes discloses the multiple treatment of a crystalline silica catalyst with an amorphous silica, such as ethylorthosilicate. Specifically, the Herkes patent contrasts the performance of a catalyst treated once with an ethylorthosilicate solution against the performance of catalyst treated twice with ethylorthosilicate. The twice-treated catalyst exhibited less selectivity than the once-treated catalyst, as measured by methylation of toluene with methanol. This indicates that multiple ex situ selectivation confers no benefit and in fact reduces a catalyst's efficacy in shape-selective reactions.

Because para-isomers of substituted aromatic hydrocarbons (e.g., para-xylene) can be utilized to produce a variety of commercial products, there is a continuing need in the art to increase the efficiency of their production. More particularly, there is a need in the art to increase the para-selectivity in alkylation reactions involving zeolites.

Accordingly, it is an object of the present invention to provide a method for increasing the para-selectivity of zeolite catalysts in alkylation reactions through the utilization of multiple ex situ treatments with a selectivating agent.

It is also an object of the present invention to provide a more efficient method of alkylating substituted aromatics to their respective para-isomers through the utilization of a multiple ex situ treated zeolite catalyst.

Moreover, it is an object of the present invention to provide a multiple ex situ treated zeolite catalyst having an increased para-selectivity in alkylation reactions.

SUMMARY OF THE INVENTION

The invention is a method for modifying a catalytic molecular sieve useful in alkylating aromatics. The modification method includes exposing a catalytic molecular sieve having a reduced alpha activity to at least two ex situ selectivation sequences. Each selectivation sequence includes contacting the catalytic molecular sieve with a selectivating agent, followed by calcination. Selectivating agents useful in the present invention include a large variety of silicon-containing compounds, preferably silicon polymers.

The selectivating agents optionally can be present in a carrier in order to facilitate the application of the selectivating agent to the catalytic molecular sieve. Preferably, the carrier is an organic carrier. Such organic carriers include various alkanes, and preferably include paraffins having 7 or more carbons.

The catalysts utilized in the present invention have a reduced alpha activity which can be achieved by either severely steaming the catalyst, ion exchanging the catalyst with an alkali metal (i.e., Group IA metal) or utilizing a catalyst with a high silica to alumina ratio. Preferably, the alpha activity level of the catalyst is reduced to less than 40, and more preferably to less than 30. In another preferred embodiment, the catalytic molecular sieve prior to being exposed to the ex situ selectivation sequences should have a constraint index between 1 and 12. In an most preferred embodiment the catalyst is ZSM-5.

The modification method of the present invention in an alternative embodiment, includes exposing a catalytic molecular sieve to at least two ex situ selectivation sequences and thereafter reducing the activity of the catalyst by ion exchange with an alkali metal.

The present invention is also a method for further modifying the modified catalytic molecular sieve by in situ trim-selectivating the modified catalytic molecular sieve. The in situ trim-selectivation can be performed by coke trim-selectivating the modified catalyst. An organic compound is decomposed in the presence of the modified catalytic molecular sieve, at conditions suitable for decomposition. Alternatively, the trim-selectivation can be performed by exposing the modified catalytic molecular sieve to a reaction stream that includes an aromatic to be alkylated, an alkylating agent and a trim-selectivating agent. Optionally, the alkylating agent can also be omitted during trim-selectivation to conserve the alkylating agent. The trim-selectivating agent is selected from a group of organic compounds which includes a large variety of silicon containing compounds.

The present invention further includes processes for shape selective alkylation of aromatics by contacting a reaction stream comprising an aromatic and an alkylating agent, under conversion conditions with a modified catalytic molecular sieve.

The alkylating agents to be utilized with the present invention include alcohols, ethers, olefins, alkyl halides and alkyl thiols. In a preferred embodiment of the present invention, an alcohol is utilized. In a more preferred embodiment of the present invention, an alcohol containing 1 to 3 carbon is utilized and most preferably, methanol. The aromatic compounds to be utilized with the present invention include any aromatic compound which can be alkylated into its para-isomer. Preferably, such aromatic compounds include monoalkylated benzenes, alkylated napthelenes and alkylated biphenyls. The most preferred aromatic compounds to be alkylated are toluene and ethylbenzene.

The present invention is also catalytic molecular sieves modified by these methods.

Advantageously, the modified catalyst has enhanced shape selectivity in the production of alkylated aromatics. Accordingly, the alkylation process of the invention exhibits increased selectivity for para-substituted isomers of the aromatics alkylated by this process.

DETAILED DESCRIPTION OF THE INVENTION

A multiple selectivation scheme for zeolite catalysts has now been discovered that provides unexpectedly better results in shape-selective aromatic alkylations than the selectivation schemes previously known. In addition, it has also now been found that a multiple selectivation scheme provides unexpectedly more efficient deposition of the selectivating agent on the zeolite catalyst than single selectivation schemes.

In accordance with the present invention, a catalytic molecular sieve (i.e., a zeolite catalyst) having a reduced alpha activity is contacted at least twice with a selectivating agent, preferably between two and six times. In an alternate embodiment of the present invention, the zeolite is contacted at least twice with a selectivating agent, preferably between two and six times, and then reduced in alpha activity.

The term "alpha activity" or "alpha value" used herein refers to the acid activity of a catalyst, which is exemplified by its catalytic cracking activity. The "alpha value" of a catalyst is an approximate indication of its catalytic cracking activity in relation to the catalytic cracking activity of a standard catalyst. The alpha value is given as a relative rate constant (the amount n-hexane converted per volume of catalyst per unit time). This relative rate constant is based on the cracking activity of a standard amorphous silica-alumina cracking catalyst which is given the alpha value of 1 (Rate Constant=0.016 sec$^{-1}$). The alpha test is described in U.S. Pat. 3,354,078 and in *The Journal of Catalysis*, Vol. 4, pp. 522–529 (August 1965); Vol. 6, p. 278 (1966); and Vol. 61, p. 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, pp. 589–591, 14 Jun. 1984). The experimental conditions of the test used herein include a constant temperature of 538° C. and a variable flow rate as described in detail in the *Journal of Catalysis*, Vol. 61, p. 395 (1980).

In accordance with the present invention, the "alpha activity" of a catalyst is reduced by either: (1) severely steaming the catalyst; (2) ion exchanging the catalyst with an alkali metal (i.e., group IA metal); or (3) using a catalyst with a high silica to alumina ratio. In a preferred embodiment of the present invention, the catalyst having a reduced activity is a catalyst with an alpha value less than 40. In a more preferred embodiment, the catalyst having a reduced activity is a catalyst with an alpha value less than 30.

In a first embodiment of the present invention, the alpha activity of the catalyst is reduced by severe steaming. In this context, severe steaming is meant to encompass steaming of a catalyst to dislodge a sufficient portion of the alumina and its associated protons within the zeolite crystal lattice thereby resulting in a decrease in the catalyst's alpha activity. For example, in a preferred embodiment of the invention, the catalyst is steamed to reduce its alpha activity to less than 40. The effect of severe steaming on a zeolite catalyst's alpha activity is illustrated in Lago, et al., "The Nature of Catalyst Sites in HZSM-5-Activity Enhancement," *Proceeding of the 7th International Zeolite Conference*, 677 (1986), which is herein incorporated by reference to the extent consistent with the present invention.

Preferably, the catalyst is treated at a steam pressure ranging from about 0.1 to about 50 atmospheres. This is done at a temperature ranging from about 700° C. to about 1100° C. The time necessary to efficate proper steaming ranges from about 0.1 to 10 hours. In a more preferred embodiment of the present invention, the catalyst is steamed with about 100% water vapor at about 0.2 to about 5 atmospheres of pressure between about 850° to about 1075° C. for about 0.1 to about 5 hours. However, as will be apparent to one skilled in the art, the previously described criteria to efficate proper steaming can vary significantly. This is especially true if the catalysts are steamed utilizing commercial scale calciners, such as those manufactured by Harper Electric Furnace Corporation.

In a second embodiment of the present invention, the catalyst's activity is reduced by ion exchange with an alkali metal (i.e., Group IA metal). This reduction in activity can be done before or after the multiple ex situ selectivation sequences. In a preferred embodiment of the present invention, the catalyst is exposed to the multiple ex situ selectivation sequences and then ion exchanged with an alkali metal.

Any method of ion exchange known in the art can be utilized in accordance with the present invention. The zeolite catalyst can be exposed to an alkali metal in its metallic form, as a salt, as a hydroxide or as an oxide. For example, the zeolite can be exposed to a liquid mixture containing at least one alkali metal which is provided in the form of a salt and hydroxide. Preferably, the catalyst is exposed to an alkali metal in the form of a salt and a hydroxide since alkali metals in these forms are widely available, are easier to handle and have a relatively low cost. The use of an alkali hydroxide increases the pH of the exchange system enhancing the exchange of protonic cations which occur within the crystal.

The alkali metals particularly preferred to be utilized with the present invention are Sodium (Na), Potassium (K) and Cesium (Cs). Examples of salts that can be utilized are NaCl, CsCl and KCl; although, any salt of an alkali metal can be used. Example of hydroxides include, but not limited to, NaOH and KOH.

In a third embodiment of the present invention, a catalyst with a reduced alpha activity is provided by utilizing a catalyst with a high silica to alumina ratio, preferably a silica to alumina ratio of at least about 200:1. In a more preferred embodiment, a catalyst having a silica to alumina ratio of about 450:1 is utilized. This ratio is meant to represent, as closely as possible, the ratio of $SiO_2$ to $Al_2O_3$ in the rigid atomic framework of the zeolite crystal excluding aluminum in the binder or in a cationic state or in other non-framework forms within the zeolite. Alternatively, the catalyst can be a boronsilicate which inherently has a high silica to alumina ratio.

In accordance with the present invention, each phase of the ex situ selectivation treatment is achieved by depositing the selectivating agent onto the external surface of the catalyst. The deposition onto the catalyst's surface can be carried out utilizing any suitable method. The selectivating agent can be a compound or a polymer containing a main group or transition metal, preferably silicon. In order to facilitate a more controlled application of the selectivating agent, the selectivating agent can be diluted in a carrier, preferably an organic carrier. For example, a silicon compound may be dissolved in a carrier, mixed with the catalyst, and then dried by evaporation or vacuum distillation. The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with a zeolite. The deposited silicon compound extensively covers, and resides substantially exclusively on, the external surface of the molecular sieve. Examples of methods of depositing silicon on the surface of the zeolite are found in U.S. Pat. Nos. 4,090,981, 4,127,616, 4,465,886 and 4,477,583 to Rodewald, which are incorporated by reference herein. Further examples of the deposition of a silicon compound on zeolite surfaces are described in H. Nakajima, M. Koya, H. Ishida, and M. Kohno, Sekiyu Gakkaishi, 35(2) (1992), and in U.S. Pat. No. 4,950,835 to Wang et al.

As described above, the catalysts of the present invention are ex situ selectivated by multiple coatings of a selectivating agent, each coating followed by calcination, and optionally the modified catalyst is trim-selectivated in situ with an additional selectivating agent. The additional selectivating agent is also referred to as the "trim-selectivating agent." As used herein, the term "selectivating agent" is used to indicate substances which will increase the para-selectivity of a catalytic molecular sieve in aromatic alkylation while maintaining commercially acceptable levels of converting the aromatic into its para-substituted isomer. Such substances include, for example, organic silicon compounds such as phenylmethyl silicone, dimethyl silicone, and blends thereof which have been found to be suitable.

Useful selectivating agents include siloxanes which can be characterized by the general formula:

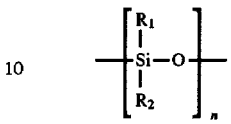

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substitutes generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, dimethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes characterizable by the general formula:

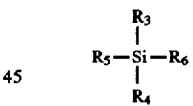

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

The preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., located in Midland, Mich.

In a preferred embodiment of the present invention, the kinetic diameter of the selectivating agent should be larger than the zeolite pore diameter. This is in order to avoid entry of the selectivating agent into the pore and any concomitant reduction in the internal activity of the catalyst.

Examples of suitable carriers for the selectivating silicon compound include linear, branched, and cyclic alkanes having five or more carbons. In the methods of the present invention, it is preferred that the carrier be a linear, branched, or cyclic alkane having a boiling point greater than about 70° C., and most preferably containing 7 or more carbons. Optionally, mixtures of low volatility organic compounds, such as hydrocracker recycle oil, may be employed as carriers. The most preferred low volatility hydrocarbon carriers of silicon selectivating agents are decane and dodecane.

It has also been found that a multiple selectivation scheme provides unexpectedly increased efficiency of deposition of the silicon compound on the surface of the catalyst. This increased efficiency allows for the use of relatively small quantities of the silicon compound as well as relatively small quantities of the optional carrier. Thus, it is believed that the present invention will provide a more economical process of depositing a selectivating agent onto a zeolite catalyst.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably, the temperature of calcination is within the approximate range of 350° C. to 550° C. The product is maintained at the calcination temperature usually for 1 to 24 hours, preferably, for 2 to 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon-coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the carrying medium, the degree to which the zeolite has been dried prior to contact with the silicon compound, and calcination of the zeolite.

During the alkylation process the aromatic may be fed simultaneously with a second selectivating agent and hydrogen at reaction conditions until the desired para-isomer selectivity, e.g., 90%, is attained. Upon attaining the desired selectivity, the co-feed of selectivating agent is discontinued. This co-feeding of selectivating agent with the aromatic is termed "in situ trim-selectivation". Reaction conditions for this in situ trim-selectivation step generally include a temperature of from about 350° C. to about 650° C. and a pressure of from about atmospheric to about 5000 psig. The reaction stream is fed to the system at a rate of from about 0.1 WHSV (weight hourly space velocity) to about 20 WHSV. Hydrogen may be fed at a hydrogen to aromatic molar ratio of from about 0.1 to about 20.

Optionally, during in situ trim-selectivation the alkylating agent can be omitted in order to conserve the alkylating agent. The alkylating agent can then be added to the reaction stream at set time intervals to determine if the catalyst has reached the desired para-selectivity. Upon reaching the desired para-selectivity, the alkylating agent is fed continuously to the reaction stream.

The selectivating agent for trim-selectivation can be a silicon compound as discussed previously. For example, organic silicon compounds such as phenylmethyl silicone, dimethyl silicone, and mixtures thereof can be utilized. In one embodiment of the present invention, a silicone mixture containing phenylmethylsilicone and dimethylsilicone in a ratio of about 1:1 is co-fed to the system, while the other components, e.g., the aromatic and hydrogen, are fed in the amounts set forth above. In a preferred embodiment of the present invention, the selectivating agent is fed in an amount ranging from about 0.001 wt. % to about 10 wt. % of the aromatic feedstock. Depending upon the percentage of selectivating agent used, the trim-selectivation will last for at least one hour, preferably about 1 to about 48 hours, more preferably less than 24 hrs.

In this scheme the silicon compound will decompose to deposit additional silica to on the catalyst. During the trim-selectivation procedure, the para-selectivity of the catalyst will be observed to increase further. The silicon-containing polymer or molecular species may be dissolved in toluene, other appropriate aromatics or an organic carrier.

Alternatively, the modified catalyst, just prior to being contacted with an aromatic under alkylation conditions, may be subjected to trim-selectivation with a thermally decomposable organic compound. This is also known as "coke trimming" the already modified catalyst. The coke trimming is done at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cyloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an aromatic, will be the source of coke, most preferably the aromatic being subjected to alkylation itself. In the latter case, the aromatic is initially brought into contact with the catalyst under conditions of temperature and hydrogen concentration amenable to rapid coke formation. Typically, coke trimming is conducted at conditions outside the operating parameters used during the main time span of the catalytic cycle. When the desired amount of coke deposition has been attained, the aromatic feed is continued in contact with the coke-containing catalyst under conditions of temperature and hydrogen concentration conducive to alkylation, with a greatly reduced coking rate.

While not wishing to be bound by theory, it is believed that the advantages of the present invention are in part obtained by rendering acid sites on the external surfaces of the catalyst substantially inaccessible to the reactants, while increasing catalyst tortuosity. Acid sites existing on the external surface of the catalyst are believed to isomerize para-isomer back to an equilibrium level with the ortho and meta isomers. In the case of xylene, the amount of para-xylene produced is reduced to about only 24%. By reducing the availability of these acid sites to the para-isomer, a relatively high proportion of the para-isomer is maintained. It is believed that the selectivating agents of the present invention block or otherwise render these external acid sites unavailable to the para-isomer of the aromatic by chemically modifying the acid sites.

Zeolites catalysts useful with the present invention have a Constraint Index, prior to ex situ selectivation, from about 1 to about 12 and include intermediate pore zeolites. These values are for the catalysts prior to ex situ selectivation since after selectivation a catalyst's Constraint Index may change. The details of the method by which Constraint Index is determined are described fully in U.S. Pat. No. 4,016,218, incorporated herein by reference. Zeolites which conform to the specified values of constraint index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,640,849, 4,046,685, 3,308,069 and Re. 28,341, to which reference is made for the details of these zeolites. The zeolite ZSM-5 is preferred for use with the present invention.

The zeolites may also be employed in combination with a support or binder material such as a porous inorganic oxide or a clay binder. The preferred binder material to be utilized is silica. Other examples of binder materials may include, but are not limited to, alumina, zirconia, magnesia, thoria, titania, boria and combinations thereof. These materials are generally provided in the form of dried inorganic oxide gels or gelatinous precipitates. Suitable clay materials include, but are not limited to, bentonite and kieselguhr. The amount of binder material combined with a zeolite to form the zeolite-binder composition ranges from about 10 to 70 wt. %, and more preferably from about 30 to 50 wt. %. The composition can be in form of an extrudate, beads or fluidizable microspheres.

The crystal size of zeolites used in accordance with the present invention is preferably greater than about 0.1 microns. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, "The Mathematics of Diffusion", Oxford at the Clarendon Press, 1957, pp 52–56, for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec.

The alkylating agents utilized with the present invention include, but are not limited to, alcohols, ethers, olefins, alkyl halides and alkyl thiols. In a preferred embodiment of the present invention, the alkylating agent is an alcohol, more preferably an alcohol containing between one to three carbons, and most preferably methanol. As will be apparent to one skilled in the art, the choice of the alkylating agent utilized is dependent on the type of alkyl substituent desired for the aromatic compound. For example, in the production of para-xylene where a methyl substituent is added, the preferred alkylating is methanol. Preferably, when methanol is utilized as the alkylating agent, water ($H_2O$) or a sulfide such as hydrogen sulfide ($H_2S$) can be co-fed to the reaction stream to passify possible decomposition of the methanol on the walls of the reactor chamber.

It is contemplated that any substituted aromatic compound, which can be converted to a para-isomer, will benefit from the present invention. Examples of substituted aromatic compounds to be utilized with the present invention include, but are not limited to, monoalkylated benzenes, alkylated napthelenes and alkylated biphenyls. Representative monoalkylated benzenes include toluene, ethyl benzene, n-propyl benzene and isopropyl benzene (cumene). Representative alkylated napthelenes include 2-methyl napthelene, 2-ethyl napthelene, 2-(n-propyl) napthelene and 2-(isopropyl) napthelene. Representative alkylated biphenyls include 4-methylbiphenyl, 4-(ethyl)biphenyl, 4-(n-propyl)biphenyl and 4-(isopropyl)biphenyl. Preferred monoalkylated benzenes utilized with the present invention are toluene and ethyl benzene.

The aromatic feedstock preferably includes about 50% to 100% aromatic, more preferably at least about 80% aromatic. Other compounds such as benzene and other substituted aromatics may also be present in the aromatic feedstock without adversely affecting the present invention.

Representative examples of the alkylation of aromatics, in which catalysts are used, are described in U.S. Pat. Nos. 3,755,483, 4,086,287, and 4,117,024 which are incorporated herein by reference.

As described in U.S. Pat. No. 3,755,483 to Burress, aromatic hydrocarbons such as benzenes, naphthalenes, anthracenes and substituted derivatives thereof, e.g., toluene and xylene, may be alkylated with alkylating agents such as olefins, ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psig, a mole ratio of aromatic/alkylating agent of from about 1:1 to about 20:1, and a WHSV of 20 to 3000 over ZSM-12 which is a ZSM-5 type catalyst.

U.S. Pat. No. 4,086,287 to Kaeding et al., describes monoalkylbenzenes having alkyls of 1–2 carbons, such as toluene and ethylbenzene, being ethylated to produce a para-ethyl derivative, e.g., para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by pre-coking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for ethylating of toluene or ethylbenzene to produce p-ethyltoluene at a temperature of 350° C. to 550° C., a critical pressure of greater than one atmosphere and less than 400 psi, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

Operating conditions employed in the process of the present invention will affect the para-selectivity and aromatic conversion. Such conditions include the temperature, pressure, weight hourly space velocity, molar ratio of the reactants, and the hydrogen to hydrocarbon mole ratio ($H_2$/HC).

EXAMPLES

The following examples illustrate the improved para-selectivity exhibited by the catalysts modified in accordance with the present invention in the alkylation of substituted cyclic aromatic compounds.

Alkylation with Catalysts Reduced in Alpha Activity by Severe Steaming

Example I

Control Catalyst 1 was prepared by exposing 5 grams of an H-ZSM-5/35% SiO$_2$ 1/16 inch extrudate to 100% water vapor at 900° C. for 2 hours. Catalyst 1 was evaluated for toluene methylation with a 1:1 toluene to methanol feed at 550° C. The reaction stream had a total feed WHSV of 3.4 and a $H_2$/toluene ratio of 1. Samples of reactor effluent were periodically analyzed by on-line gas chromatography. The liquid product was collected in a cold trap cooled to −5° C. Samples of the liquid product collected were also analyzed by gas chromatography. The analysis of a sample of the liquid product collected over 16 hours is shown in Table 1.

TABLE 1

| Toluene Conversion (Wt %) | 42.17% |
|---|---|
| Total Xylene | 35.84% |
| Meta | 9.57% |
| ortho | 7.19% |
| Para | 19.08% |
| Para-Selectivity (Wt %) | 53% |

Example II

Test Sample 2 was produced by contacting 3.95 grams of Control Catalyst 1 with a solution of 0.702 grams Dow-550 dissolved in 13 grams dodecane. The dodecane was stripped off the catalyst using nitrogen ($N_2$) at 210°–220° C. The catalyst was subsequently calcined in a muffle furnace under a mixture of 80%/20% $N_2$:air flowing at 60 cc/min. The temperature was elevated at 2° C./min. until 538° C. and maintained at that temperature for 6 hours.

Sample 2, which now contained approximately 10% wt of added silica, was evaluated with a 1:1 toluene to methanol feed at 550° C. The reaction stream had a 6.8 WHSV, 100 psig and a 10:1 $H_2$/toluene ratio. The reaction effluent and the liquid product collected were analyzed using the procedure of Example I. The analysis of a sample of the liquid product collected over 11 hours utilizing this once-selectivated catalyst is shown in Table 2.

TABLE 2

| Toluene Conversion (Wt. %) | 28.7% |
|---|---|
| Total Xylene | 23.10% |
| Meta | 2.50% |
| Ortho | 1.90% |
| Para | 18.70% |
| Para-Selectivity (Wt. %) | 81.0% |

Example III

Test Sample 3 was produced by contacting 2.96 grams of Sample 2 with a solution of 0.52 grams Dow 550 dissolved in 10 grams dodecane. The catalyst was subsequently calcined using the procedure in Example II.

Sample 3, which now contains approximately 20% Wt. of added silica, was first evaluated on a reaction stream containing a 1:1 toluene to methanol feed at 550° C., at 3.4 WHSV, 60 PSIG and a 20:1 $H_2$/toluene ratio. After four hours on line, samples of the reaction effluent and of the liquid product collected were analyzed. The reaction was continued at 100 psig for an additional 15 hours. A sample of the liquid product collected after 19 hours on-line was also analyzed. The results from the samples of liquid product collected are shown in Table 3.

TABLE 3

|  | 4 hrs. | 19 hrs. |
|---|---|---|
| Toluene Conversion (Wt. %) | 20.56% | 19.47% |
| Total Xylene (Wt. %) | 11.40% | 17.92% |
| Meta | 0.93% | 0.54% |
| Ortho | 0.57% | 0.27% |
| Para | 17.10% | 17.11% |
| Para-Selectivity (Wt. %) | 91.9% | 95.5% |

Alkylation With Catalysts Reduced In Alpha Activity By Ion Exchange With An Alkali Metal Example IV Control Catalyst 4 was prepared by exposing 50.1 grams of HZSM-5/SiO$_2$ (1/16 inch extrudate, dried at 105° C.) to a solution of 4.62 grams Dow 550 dissolved in 40 grams dodecane. The catalyst was allowed to contact and adsorb the silicone solution for several minutes after which the dodecane was stripped from the catalyst under nitrogen ($N_2$) at 210°–220° C. The catalyst was then placed in a metal box and calcined in a muffle furnace in which temperature was increase by 2° C./minute until 538° C. in a 80%/20% $N_2$/air mixture flowing at 60 cc/minute. The catalyst was calcined at 538° C. for about 4 hrs. the catalyst was then cooled under $N_2$ and was weighed to determine the amount of weight gained from the silica added. The amount of silica added was 2.6 wt. %.

The once-selectivated catalyst, now weighing 50.4 grams, was subsequently contacted with a solution of 4.64 grams of Dow 550 dissolved in 40 grams dodecane. The catalyst was then stripped and calcined according to procedure previously stated. The catalyst, now twice-selectivated, was found to have gained 3.2 wt. % in silica.

The twice-selectivated catalyst, now weighing 51.0 grams, was contacted with a solution of 1.9 grams Dow 550 dissolved in 40 grams dodecane. The catalyst was stripped and calcined using the procedure previously stated. The catalyst, now three-times selectivated, was found to have gained 2.1 wt. % from silica addition. Thus, the total amount of weight gain due to silica addition was 8.0 wt. %.

One gram of this three times-selectivated catalyst was evaluated for toluene methylation. A feed stream with a 0.15 molar methanol to toluene feed at 500° C. and 60 PSIG was used. The stream was fed at a rate of 8 ml/hr., and at 10 cc/minute $H_2$ co-feed. Significant catalyst aging was observed due to the high catalyst acidity (alpha activity). As a result of the severe aging of the catalyst the exact concentrations of the para and meta isomers could not be determined since no liquid product could be collected due to the catalyst aging. A sample of the reactor effluent at 2 hours on-line was analyzed by on-line gas chromatograph. A meta and para/ortho ratio of 71 was observed which is indicative of high para-selectivity. The analysis of a sample of the reaction effluent collected is shown in Table 4.

TABLE 4

| Toluene Conversion (Wt. %) | 5.49% |
|---|---|
| Total Xylene (Wt. %) | 2.66% |
| Ortho | .04% |
| Para + Meta | 2.62% |
| Para Selectivity (Wt. %) | N/A |

Example V

Test Sample 5 was prepared by exposing 2.1 grams of the three-times selectivated catalyst of Example IV to a mixture of 25 ml. 0.1M NaCl (pH 3.10), 5 ml. 1M CsCl (pH 2.65), and 0.9 ml. 0.1M NaOH (pH 4.10). The catalyst was stirred in this mixture in order to reduce the pH of the catalyst and thereby facilitated an exchange of ions within the zeolite. The mixture left overnight exhibited a pH of 3.22. The catalyst was then filtered, washed and dried. The catalyst was evaluated for toluene methylation with a 1:1 toluene to methanol feed at 550° C., 3.4 WHSV, 50 PSIG, and a H$_2$/toluene ratio of 1. Severe aging of the catalyst was not observed, as was observed with control catalyst 4. The analysis of a sample of the liquid product collected after the first 2 hours of on-line is shown in Table 5.

TABLE 5

| Toluene Conversion (Wt. %) | 9.77% |
|---|---|
| Total Xylene (Wt. %) | 8.31% |
| Meta | 0.28% |
| Ortho | 0.35% |
| Para | 7.68% |
| Para-Selectivity (Wt. %) | 92.4% |

Alkylation with Catalysts Having a High Silica to Alumina Ratio

Example VI

Control Sample 6, HZSM-5(450), was evaluated for toluene methylation. The catalyst has a silica to alumina ratio of 450:1 and an alpha value of 34. The catalyst was exposed to a feed stream with a 11.3:1 toluene:methanol ratio at 500° C., 100 PSIG, a H$_2$/toluene ratio of 1 and a WHSV of 8. The analysis of a sample of the liquid product collected is shown in Table 6.

TABLE 6

| Toluene Conversion (Wt. %) | 10.60% |
|---|---|
| Total Xylene (Wt. %) | 8.50% |
| Meta | 4.50% |
| Ortho | 1.97% |

TABLE 6-continued

| Para | 2.03% |
|---|---|
| Para-Selectivity (Wt. %) | 23.9% |

Example VII

Test Sample 7 was prepared by contacting 10.46 grams of HZSM-5(450) in Example VI with a 7.58 wt. % Dow 550 in decane solution in a ratio of 1.2 grams of solution/gram of solid catalyst. The resulting thick slurry was mixed for approximately 10 minutes at room temperature. The catalyst was programmed calcined in flowing nitrogen at 540° C. for 2 hours, thereafter cooled to 300° C. and then programmed calcined to 540° C. in flowing air for about another 4 hours. This procedure of silica addition and calcination was repeated two more times. The catalyst exhibited an alpha value of 20.

The above stated catalyst, which is three-times selectivated, was evaluated for methylation of toluene. The catalyst was contacted with a feed stream having a 8:1 toluene to methanol ratio at 500° C., 40 PSIG, a H$_2$/toluene ratio of 8 and a WHSV of 10. Samples of the reactor effluent and liquid product collected were analyzed according to the procedure utilized in Example I. The analysis of the sample of liquid product collected is shown in Table 7.

TABLE 7

| Toluene Conversion (Wt. %) | 10.3% |
|---|---|
| Total Xylene (Wt. %) | 9.47% |
| Meta | 1.42% |
| Ortho | 0.44% |
| Para | 7.61% |
| Para-Selectivity (Wt. %) | 80.4% |

Example VIII

Test Sample 8 was prepared by contacting 4.92 grams of the three-times treated catalyst of Example VII with a 4.55 wt. % Dow 550 in decane solution in a ratio of 1.25 grams of solution/gram of solid catalyst. The catalyst was calcined using the procedure described in Example VII. The catalyst, now four-four times selectivated, exhibited an alpha value of 27.

Test Sample 8, was evaluated for toluene methylation. The catalyst was contacted with a 8:1 toluene:methanol feed at 500° C., 40 PSIG, a H$_2$/toluene ratio of 4 and a WHSV of 10. After 12.3 hours on-line, samples of the reactor effluent and of the liquid product collected were analyzed according to the procedure described in Example I. The catalyst was then allowed to remain on-line for a total of 28.4 hrs. at 550° C. and a WHSV of 5. Samples of the reactor effluent and of the liquid product collected were also taken and analyzed. The analysis of the samples of the liquid product collected is shown in Table 8.

TABLE 8

|  | 12.3 hrs. | 28.4 hrs. |
|---|---|---|
| Toluene Conversion (Wt. %) | 9.74% | 8.40% |
| Total Xylene (Wt. %) | 8.58% | 7.58% |
| Meta | 1.00% | .37% |
| Ortho | 0.29% | 0.04% |
| Para | 7.29% | 7.17% |
| Para-Selectivity (Wt. %) | 85.0% | 94.6% |

Comparative Para-Selectivities of Examples I–VIII

TABLE 9

| Catalyst | Number of Ex-Situ Selectivation Treatments | Para-Selectivity |
|---|---|---|
| Control 1 | 0 | 53.% |
| Test Sample 2 | 1 | 81.0% |
| Test Sample 3 | 2 | 95.5% |
| Control 6 | 0 | 23.9% |
| Test Sample 6 | 3 | 80.4% |
| Test Sample 7 | 4 | 94.6% |

As can be seen from Table 9, the combination of multiple ex situ selectivation sequences and reduction in activity resulted in an increase in the para-selectivity of the zeolite catalysts. The increase in para-selectivity was determined by comparing the amount of para-xylene produced as a percentage of total xylene produced through the methylation of toluene. Specifically, by comparing the para-selectivities of Test Sample 2 which was selectivated only once, with test sample 3, which was selectivated twice, an improvement in the para-selectivity of the catalyst was observed. This improvement is attributable to the multiple ex situ selectivation treatment of catalyst. This was unexpected because one skilled in the art would not have expected the para-selectivity of Test Sample 3, which was 95.5%, to have been greater than the para-selectivity of Test Sample 2, which was 81.0%. The skilled artisan would have expected to Test Sample 3 to have a para-selectivity less than 81% since a decrease in para-selectivity was observed when multiple ex situ treatments were utilized in the prior art.

The advantages of multiple ex situ treatments can be further observed by comparing Test Sample 7, which had para-selectivity of 80.4%, to Test Sample 8, which had a para-selectivity of 94.6%. The difference in para-selectivity is also attributable to the one extra ex situ selectivation treatment of the catalyst Test Sample 8.

Therefore, the use of multiple ex situ treatments combined with a reduction in the catalyst's alpha activity unexpectedly provides an increase in para-selectivity. This was observed from the increased selectivity for the para-isomers of aromatics alkylated utilizing the catalysts of the present invention.

Thus, while there have been described what are presently believed to be the preferred embodiments of the invention, those skilled in the art will realize that various changes and modifications may be made to the invention without departing from the spirit of such invention. All such changes and modifications will fall within the scope of the invention and therefore intended to be claimed.

We claim:

1. A method for alkylation of aromatics which comprises:
    contacting a reaction stream including an aromatic and an alkylating agent, with a zeolite catalyst having a constraint index ranging from about 1 to about 12 and an alpha activity less than about 40, which has been modified by being exposed to at least two ex situ selectivation sequences, wherein said ex situ selectivation sequence includes the steps of depositing on said zeolite catalyst a selectivating agent selected from the group consisting of silicones and silicone polymers and, subsequently calcining said zeolite catalyst.

2. The method of claim 1, wherein said aromatic is a monoalkylated benzene.

3. The method of claim 2, wherein said monoalkylated benzene is selected from the group consisting of ethyl benzene, n-propyl benzene and isopropyl benzene (cumene).

4. The method of claim 2, wherein said monoalkylated benzene is toluene.

5. The method of claim 1, wherein said aromatic is an alkylated napthelene.

6. The method of claim 5, wherein said alkylated napthelene is selected from the group consisting of 2-methyl napthelene, 2-ethyl napthelene, 2-(n-propyl) napthelene and 2-(isopropyl) napthelene.

7. The method of claim 1, wherein said aromatic is an alkylated biphenyl.

8. The method of claim 7, wherein said alkylated biphenyl is selected from the group consisting of 4-methylbiphenyl, 4-(ethyl)biphenyl, 4-(n-propyl)biphenyl and 4-(isopropyl) biphenyl.

9. The method of claim 1, wherein said alkylating agent is selected from the group consisting of ethers, olefins, alkyl halides and alkyl thiols.

10. The method of claim 1, wherein said alkylating agent is an alcohol.

11. The method of claim 10, wherein said alcohol is an alcohol containing 1 to 3 carbons.

12. The method of claim 11, wherein said alcohol is methanol.

13. A method for modifying a zeolite catalyst for shape selective aromatic alkylation which comprises:
    providing a zeolite catalyst having a constraint index ranging from about 1 to about 12 and having an alpha activity less than about 40; and
    exposing said zeolite catalyst to at least two ex situ selectivation sequences, wherein said ex situ selectivation sequence includes the steps of:
    depositing on said zeolite catalyst a selectivating agent selected from the group consisting of silicones and silicone polymers and;
    subsequently calcining said zeolite catalyst.

14. The method of claim 1, wherein said zeolite catalyst has been modified by two ex situ selectivation sequences.

15. The method of claim 13, wherein said zeolite catalyst is a zeolite catalyst having an alpha activity level less than about 30.

16. The method of claim 13, wherein said zeolite catalyst is a zeolite catalyst having been steamed.

17. The method of claim 16, wherein said zeolite catalyst is steamed at a temperature from about 700° C. to about 1100° C.

18. The method of claim 16, wherein said zeolite catalyst is steamed at a pressure ranging from about 0.1 atmospheres to about 100 atmospheres.

19. The method of claim 16; wherein said zeolite catalyst is steamed from about 0.01 hours to about 10 hours.

20. The method of claim 13, wherein said zeolite catalyst is a zeolite catalyst having been ion exchanged with an alkali metal.

21. The method of claim 20, wherein said alkali metal is selected from the group consisting of sodium, potassium, cesium and mixtures thereof.

22. The method of claim 13, wherein said zeolite catalyst is a zeolite catalyst having a silica to alumina ratio of at least about 200:1.

23. The method of claim 22, wherein said zeolite catalyst is a zeolite catalyst having a silica to alumina ratio of at least about 450:1.

24. The method of claim 13, wherein said zeolite catalyst is a zeolite catalyst selected from the group consisting of ZSM-11, ZSM-5/ZSM-11 intermediate, ZSM-12, ZSM-22, ZSM-23, ZSM-35, ZSM-48, ZSM-50 and ZSM-57.

25. The method of claim 13, wherein said zeolite catalyst is ZSM-5.

26. The method of claim 13, wherein said selectivating agent is selected from the group consisting of

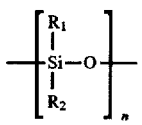

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000.

27. The method of claim 1, wherein said selectivating agent comprises dimethylphenylmethyl polysiloxane.

28. The method of claim 1, wherein said selectivating agent comprises phenylmethyl polysiloxane.

29. The method of claim 13, wherein said selectivating agent is present in an organic carrier prior to contacting said zeolite catalyst.

30. The method of claim 29, wherein said organic carrier comprises a linear, branched, or cyclic hydrocarbon.

31. The method of claim 29, wherein said organic carrier is a paraffin containing at least 7 carbon atoms.

32. The method of claim 29, wherein said organic carrier is selected from the group consisting of heptane, octane, nonane, decane, undecane and dodecane.

33. The method of claim 29, wherein said organic carrier comprises hydrocracker recycle oil.

34. The method of claim 13, further comprising the step of in situ trim-selectivating said modifies zeolite catalyst.

35. The method of claim 34, wherein said in situ trim-selectivating step comprises contacting said modified zeolite catalyst with a thermally decomposable organic compound selected from the group consisting of paraffins, cycloparaffins, olefins, cycloolefins, aromatics, alcohols, aldehydes, ethers, ketones, phenols, heterocyclics, and mixtures thereof, at a temperature in excess of the decomposition temperature of said thermally decomposable organic compound.

36. The method of claim 34, wherein said in situ trim-selectivating step comprises contacting said modified zeolite catalyst with a reaction stream including an aromatic, an alkylating agent and a trim-selectivating agent, at reaction conditions for alkylation of said aromatic.

37. The method of claim 36, wherein said trim-selectivating agent is selected from the group consisting of silicones, silicone polymers, silanes, and alkoxysilanes.

38. The method of claim 36, wherein said trim-selectivating agent is selected from the group consisting of

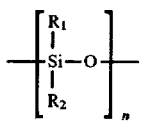

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and

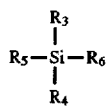

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

39. The method of claim 36, wherein said trim-selectivating agent comprises dimethylphenylmethyl polysiloxane.

40. The method of claim 36, wherein said trim-selectivating agent comprises phenylmethyl polysiloxane.

41. The method of claim 36, wherein said aromatic is a monoalkylated benzene.

42. The method of claim 41, wherein said monoalkylated benzene is selected from the group consisting of ethyl benzene, n-propyl benzene and isopropyl benzene (cumene).

43. The method of claim 41, wherein said monoalkylated benzene is toluene.

44. The method of claim 36, wherein said aromatic is an alkylated napthelene.

45. The method of claim 36, wherein said alkylated napthelene is selected from the group consisting of 2-methyl napthelene, 2-ethyl napthelene, 2-(n-propyl) napthelene and 2-(isopropyl) napthelene.

46. The method of claim 36, wherein said aromatic is an alkylated biphenyl.

47. The method of claim 46, wherein said alkylated biphenyl is selected from the group consisting of 4-methylbiphenyl, 4-(ethyl)biphenyl, 4-(n-propyl)biphenyl and 4-(isopropyl)biphenyl.

48. A method for modifying a zeolite catalyst for shape selective aromatic alkylation which comprises:
exposing a zeolite catalyst having a constraint index ranging from about 1 to about 12 to at least two ex situ selectivation sequences, wherein said ex situ selectivation sequence includes the steps of depositing on said zeolite catalyst a selectivating agent selected from the group consisting of silicones and silicone polymers and, subsequently calcining said zeolite catalyst; and
reducing the alpha activity of said zeolite catalyst to an alpha activity level less than about 40 by ion exchange with an alkali metal.

49. The method of claim 48, wherein said zeolite catalyst is reduced in alpha activity to an alpha activity level less than about 30.

50. The method of claim 48, wherein said zeolite catalyst is a zeolite catalyst selected from the group consisting of ZSM-11, ZSM-5/ZSM-11 intermediate, ZSM-12, ZSM-22, ZSM-23, ZSM-35, ZSM-48, ZSM-50 and ZSM-57.

51. The method of claim 48, wherein said zeolite catalyst is ZSM-5.

52. The method of claim 48, wherein said alkali metal is selected from the group consisting of sodium, potassium, cesium and mixtures thereof.

53. The method of claim 48, wherein said selectivating agent is selected from the group consisting of

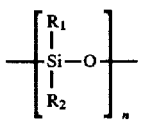

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkary, and halogenated alkaryl, and n is between 2 and 1000.

54. The method of claim 48, wherein said selectivating agent comprises dimethylphenylmethyl polysiloxane.

55. The method of claim 48, wherein said selectivating agent comprises phenylmethyl polysiloxane.

56. The method of claim 48, wherein said organic carrier comprises a linear, branched, or cyclic hydrocarbon.

57. The method of claim 48, wherein said selectivating agent is present in an organic carrier prior to contacting said zeolite catalyst.

58. The method of claim 57, further comprising the step of in situ trim-selectivating said modified zeolite catalyst.

59. The method of claim 58, wherein said in situ trim-selectivating step comprises contacting said modified zeolite catalyst with thermally decomposable organic compound selected from the group consisting of paraffins, cycloparaffins, olefins, cycloolefins, aromatics, alcohols, aldehydes, ethers, ketones, phenols, heterocyclics, and mixtures thereof, at a temperature in excess of the decomposition temperature of said thermally decomposable organic compound.

60. The method of claim 58, wherein said in situ trim-selectivating step comprises contacting said modified zeolite catalyst with a reaction stream including an aromatic, an alkylating agent and a trim-selectivating agent, at reaction conditions for alkylation of said aromatic.

61. The method of claim 60, wherein said trim-selectivating agent is selected from the group consisting of silicones, silicone polymers, silanes and alkoxysilanes.

62. The method of claim 60, wherein said trim-selectivating agent is selected from the group consisting of

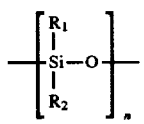

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, aklaryl, and halogenated alkaryl, and n is between 2 and 1000; and

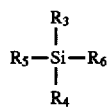

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

63. The method of claim 60, wherein said trim-selectivating agent comprises dimethylphenylmethyl polysiloxane.

64. The method of claim 60, wherein said trim-selectivating agent comprises phenylmethyl polysiloxane.

65. The method of claim 60, wherein said aromatic is a monoalkylated benzene.

66. The method of claim 65, wherein said monoalkylated benzene is selected from the group consisting of ethyl benzene, n-propyl benzene and isopropyl benzene (cumene).

67. The method of claim 65, wherein said monoalkylated benzene is toluene.

68. The method of claim 60, wherein said aromatic is an alkylated napthelene.

69. The method of claim 68, wherein said alkylated napthelene is selected from the group consisting of 2-methyl napthelene, 2-ethyl napthelene, 2-(n-propyl) napthelene and 2-(isopropyl) napthelene.

70. The method of claim 60, wherein said aromatic is an alkylated biphenyl.

71. The method of claim 70, wherein said alkylated biphenyl is selected from the group consisting of 4-methylbiphenyl, 4-(ethyl)biphenyl, 4-(n-propyl)biphenyl and 4-(isopropyl)biphenyl.

72. The method of claim 57, wherein said organic carrier is a paraffin containing at least 7 carbon atoms.

73. The method of claim 57, wherein said organic carrier is selected from the group consisting of heptane, octane, nonane, decane, undecane and dodecane.

74. The method of claim 57, wherein said organic carrier comprises hydrocracker recycle oil.

75. A modified zeolite catalyst for shape selective aromatic alkylation which has been prepared by exposing a zeolite catalyst having a constraint index from about 1 to about 12 and having an alpha activity less than about 40, to at least two ex situ selectivation sequences, wherein said ex situ selectivation sequence includes the steps of:

depositing on said zeolite catalyst a selectivating agent selected from the group consisting of silicones and silicon polymers and;

subsequently calcining said zeolite catalyst.

76. A modified zeolite catalyst for shape selective aromatic alkylation which has been prepared by exposing a zeolite catalyst having a constraint index ranging from about 1 to about 12 to at least two ex situ selectivation sequences, wherein said ex situ selectivation sequence includes the steps of depositing on said zeolite catalyst a selectivating agent selected from the group consisting of silicones and silicone polymers and subsequently calcining said zeolite catalyst thereafter reducing the alpha activity of said selectivated zeolite catalyst to less than about 40 by ion exchange with an alkali metal.

* * * * *